United States Patent [19]

Zemlanicky et al.

[11] Patent Number: 5,001,270
[45] Date of Patent: Mar. 19, 1991

[54] PROCESS FOR RECOVERING 4,4′ DIHYDROXYDIPHENYL SULFONE FROM AN ISOMER MIXTURE

[75] Inventors: Fred Zemlanicky, Hillside; Bernard Cooker, Piscataway, both of N.J.

[73] Assignee: Amoco Corporation, Chicago, Ill.

[21] Appl. No.: 299,116

[22] Filed: Jan. 18, 1989

Related U.S. Application Data

[63] Continuation of Ser. No. 904,803, Sep. 8, 1986, abandoned, which is a continuation of Ser. No. 784,041, Oct. 4, 1985, abandoned.

[51] Int. Cl.$^5$ ............................................. C07C 315/06
[52] U.S. Cl. ...................................................... 568/33
[58] Field of Search ........................................... 568/33

[56] References Cited

U.S. PATENT DOCUMENTS

| | | | |
|---|---|---|---|
| 2,392,137 | 1/1946 | Foster | 568/33 |
| 2,833,828 | 5/1958 | Sauls | 568/33 |
| 3,065,274 | 11/1962 | Vegter et al. | 568/33 |
| 3,277,183 | 10/1966 | Heller et al. | 568/33 |
| 3,297,766 | 1/1967 | Bradley et al. | 568/33 |
| 3,366,692 | 1/1968 | Orem | 568/33 |
| 3,551,501 | 12/1970 | Clark | 568/33 |
| 4,113,974 | 9/1978 | Mark et al. | 568/33 |
| 4,162,270 | 7/1979 | Ogata et al. | 568/33 |
| 4,324,926 | 4/1982 | Demler et al. | 568/730 |
| 4,382,147 | 5/1983 | Kitamura | 568/33 |

FOREIGN PATENT DOCUMENTS

| | | | |
|---|---|---|---|
| 165526 | 2/1953 | Australia | 568/33 |
| 50-11644 | 6/1975 | Japan | 568/33 |
| 4324660 | 9/1975 | Japan | 568/33 |
| 51-52153 | 5/1976 | Japan | 568/33 |
| 51-98239 | 8/1976 | Japan | 568/33 |
| 57-38765 | 3/1982 | Japan | 568/33 |
| 225157 | 12/1984 | Japan | 568/33 |
| 2030566 | 4/1980 | United Kingdom | 568/33 |

OTHER PUBLICATIONS

Hinkel and Summers, 4:4′-and 2:4′-Dihdyroxydiphenyl Sulfones, *Chemical Society Journal* (1949) p. 2854.

*Primary Examiner*—Mary E. Ceperley
*Attorney, Agent, or Firm*—Janice M. McLain; William H. Magidson; Ralph C. Medhurst

[57] ABSTRACT

A process for recovering 4,4′ bisphenol sulfone from an isomer mixture comprising the 4,4′ and 2,4′ isomers of bisphenol sulfone, which process comprises dissolving the isomer misture in a basic aqueous solution and adding a non-neutralizing amount of acid to selectively precipitate crystals of 4,4′ bisphenol sulfone.

8 Claims, No Drawings

PROCESS FOR RECOVERING 4,4' DIHYDROXYDIPHENYL SULFONE FROM AN ISOMER MIXTURE

This is a continuation, of application Ser. No. 06/904,803, filed Sept. 8, 1986, abandoned which is a continuation of Ser. No. 06/784,041, filed Oct. 4, 1985, abandoned.

FIELD OF THE INVENTION

This invention relates to the recovery of 4,4' bisphenol sulfone (4,4' dihydroxydiphenyl sulfone) from an isomer mixture of bisphenol sulfones. More particularly, this invention relates to the recovery of 4,4' bisphenol sulfone by aqueous recrystallization from a mixture comprising the 4,4' and 2,4' isomers of bisphenol sulfone.

BACKGROUND OF THE INVENTION 4,4' bisphenol sulfone (4,4' dihydroxydiphenyl sulfone) has found particular utility as a monomer in the production of high molecular weight polymers such as polyphenylsulfone resins. For such use, however, 4,4' bisphenol sulfone must be substantially free of its 2,4' bisphenol sulfone isomer and be of high purity in order to yield a quality polymer product. Polymers made from 4,4' bisphenol sulfone having an appreciable amount of 2,4' isomer generally do not reach as high a molecular weight and do not exhibit mechanical properties as excellent as polymers made from purified 4,4' bisphenol sulfone. As little as 2 percent impurity can cause the 4,4' bisphenol sulfone to be unsatisfactory as a monomer for certain polymerizations.

Commercial processes generally have not been able to synthesize 4,4' bisphenol sulfone of sufficient purity for its general application as a polymerization monomer. Almost invariably 4,4' bisphenol sulfone is formed in admixture with undesirably large amounts of its 2,4' isomer. Depending on the method of its synthesis, 4,4' bisphenol sulfone also may contain minor amounts of a variety of other impurities such as phenol, phenol sulfonic acid, quinone-type coloring agents, resins and tars.

Accordingly, the literature is replete with descriptions of proposed methods for recovering 4,4' bisphenol sulfone from mixtures of 4,4' and 2,4' bisphenol sulfone. Proposed recovery methods include various processes using organic solvents to extract the 2,4' isomer and recover the undissolved 4,4' isomer from isomer mixtures of bisphenol sulfone. For example, there have been described solvent extraction methods using ethers (U.S. Pat. No. 2,833,828), S-tetrachloroethane (U.S. Pat. No. 3,065,274) and esters (U.S. Pat. No. 3,551,501). These methods, however, generally require a high temperature solvent extraction step, followed by a solvent wash step, and then a recrystallization step to recover purified 4,4' bisphenol sulfone from the bisphenol sulfone mixture. This succession of steps inevitably results in substantial loss of 4,4' bisphenol sulfone, as well as solvent, thereby rendering the methods commercially unacceptable.

Recovery of 4,4' bisphenol sulfone by recrystallization from water also has been often proposed. Due to the low solubility of bisphenol sulfone in water, the described methods employ heated solutions of alkali (U.S. Pat. No. 4,162,270) or convert bisphenol sulfone to an alkali metal salt (U.S. Pat. No. 3,297,666) in order to more readily achieve an aqueous solution to which is added activated carbon that adsorbs impurities. After filtration, the aqueous solution is neutralized or acidified and the bisphenol sulfone recrystallizes. These recrystallization methods, however, are only effective in recovering 4,4' bisphenol sulfone product free from by-product coloring agents and resinous impurities, as substantial amounts of 2,4' isomer precipitate along with the 4,4' isomer.

Other aqueous recrystallization methods that have been proposed for recovering 4,4' bisphenol sulfone are described as involving the formation and heat dissolution of a calcium complex (U.S. Pat. No. 2,392,137) or an alkali-metal complex (U.S. Pat. No. 3,277,183) which precipitate upon cooling of the solution. These methods, though they are said to be effective in removing some 2,4' isomer, nevertheless coprecipitate 2,4' bisphenol sulfone in amounts such that successive recrystallizations are required to recover 4,4' bisphenol sulfone of high purity. Again the succession of steps results in unacceptable product loss.

SUMMARY OF THE INVENTION

This invention relates to a process for the recovery of 4,4' bisphenol sulfone from an isomer mixture comprising the 4,4' and 2,4' isomers of bisphenol sulfone, which process comprises dissolving the isomer mixture in a basic aqueous solution to form an isomer solution and adding acid to the isomer solution to selectively precipitate crystals of 4,4' bisphenol sulfone. The amount of acid added to the solution is sufficient to cause significant precipitation of crystals of 4,4' bisphenol sulfone but is an amount less than sufficient to neutralize the isomer solution. In a preferred embodiment, less than 1 equivalent of acid is added per mole of the 4,4' bisphenol sulfone.

In not neutralizing or acidifying the isomer solution, the 2,4' isomer and other impurities substantially remain dissolved, while the 4,4' bisphenol sulfone precipitates in significant quantity from the aqueous solution rendered less basic by the acid addition. Accordingly, by the recovery process of the present invention, 4,4' bisphenol sulfone is recovered in high purity from a single aqueous recrystallization of an isomer mixture containing 4,4' and 2,4' bisphenol sulfone.

The recovery process is highly selective in recovering 4,4' bisphenol sulfone with minimal amounts of 2,4' bisphenol sulfone and other impurities and by-products. Because highly pure 4,4' bisphenol sulfone can be recovered without a succession of recrystallization and purification steps, product loss is minimal. Thus, the recovery process of this invention is efficient and economical for commercial operations.

DETAILED DESCRIPTION OF THE INVENTION

It has been found that 4,4' bisphenol sulfone of high purity, typically at least 98 percent pure, is obtained from isomer mixtures of 4,4' and 2,4' bisphenol sulfone by use of the recovery process according to the present invention. The present invention involves the following steps. First, the isomer mixture of 4,4' and 2,4' bisphenol sulfone is fully or nearly fully dissolved in a basic aqueous solution. Then, acid is added to the resulting isomer solution in an amount which is less than sufficient to neutralize the solution, yet is an amount sufficient to selectively precipitate a major portion of the 4,4' bisphenol sulfone as purified crystals. Typically, the amount of acid added is less than one equivalent per mole of the 4,4' bisphenol sulfone contained in the dissolved isomer mixture. The precipitate of purified 4,4' bisphenol sulfone is then separated from the solution by filtration, centrifugation or other similar techniques.

The isomer mixture of bisphenol sulfone from which 4,4' bisphenol sulfone is to be recovered generally should contain at least about 75 percent and preferably at least about 90 percent by weight 4,4' bisphenol sulfone. Recovery of 4,4' bisphenol sulfone from isomer mixtures containing lesser amounts of 4,4' bisphenol sulfone can be accomplished according to the process of the present invention, though the recovery process may have to be repeated in order to obtain 4,4' bisphenol sulfone of the desired high purity.

The recovery process can also be applied to isomer mixtures of bisphenol sulfone in which the solvent used in its synthesis has not been yet completely removed. With such mixtures the solvent is removed during the recovery process. For example, in the use of this process to recover 4,4' bisphenol sulfone from an isomer mixture of bisphenol sulfones prepared from the reaction of sulfuric acid and phenol in the presence of dichlorobenzene solvent, any solvent remaining in the product mixture segregates as a separate organic layer when mixed in the basic aqueous solution. Dichlorobenzene is essentially immiscible with the aqueous phase while bisphenol sulfone and its impurities are readily extracted from the dichlorobenzene into the aqueous layer. The solvent layer is then removed by conventional means such as decanting or similar means.

Dissolution of mixtures of 2,4' and 4,4' bisphenol sulfone is achieved by mixing the isomer mixture with a basic aqueous solution at elevated temperatures. The temperature of the solution is not critical. However, the higher the solution temperature, the more readily the bisphenol sulfone dissolves. Generally the temperature should be at least about 60° C. to effect complete dissolution. Temperatures at or above the boiling point of the basic aqueous solution usually should be avoided because of the normal problems attendant with vaporization of the solution. In addition, at excessively high temperatures, the caustic might react with the bisphenol sulfone to produce quinone-type impurities. This reaction is undesirable not only because bisphenol is consumed but also because such impurities impart color to the final product. Thus the temperature of the basic aqueous solution normally should be maintained below but near its boiling point, preferably between about 90° and 100° C.

The amount of basic aqueous solution employed in the recovery of purified 4,4' bisphenol sulfone is not critical as long as there is sufficient quantity to dissolve all of the 2,4' bisphenol sulfone impurity present in the isomer mixture and sufficient quantity to dissolve both of the isomers at the elevated temperature of the solution. Preferably, the quantity of basic aqueous solution is such that, upon complete dissolution, the concentration of the dissolved bisphenol sulfone isomers in the solution will be about 10 to 50 weight percent. The use of appreciably lesser amounts of water may present mechanical handling problems in commercial operations, while the use of significantly greater amounts of water bestows no significant benefit.

The concentration of base in the aqueous solution is similarly not critical as long as it is sufficient to cause the bisphenol sulfone isomers to dissolve in the basic aqueous solution at the elevated temperature employed. Normally, base present in an amount to provide about one equivalent of base per mole of bisphenol sulfone (calculated on the total amount of both the 4,4' and 2,4' isomers) is sufficient to fully dissolve the bisphenol sulfone isomers. With this amount of base, the pH of the aqueous isomer solution is generally about 11. Additional base, of course, may be added as needed to obtain complete dissolution of the bisphenol sulfone isomers. Excessive amounts of base, however, provide no appreciable benefit and might, over time, react with the bisphenol sulfone to form unwanted impurities.

Suitable bases include, for example, alkali-metal hydroxides, carbonates, bicarbonates, and alkaline-earth-metal hydroxides, mixtures thereof, and the like. A strong, well-dissociated, and inexpensive, base such as sodium hydroxide is preferred.

As an optional constituent, a water soluble alcohol may be employed in the basic aqueous solution in which the isomer mixture of bisphenol sulfone is dissolved. The presence of alcohol in the basic solution tends to dissolve the quinone-type coloring agents and prevent them from precipitating with the 4,4' bisphenol sulfone upon the addition of acid. The result is that the recovered 4,4' bisphenol sulfone has an improved (i.e. whiter) color which is preferred by the industry. As the alcohol also will tend to keep 4,4' bisphenol sulfone in solution, the amount of alcohol that may be employed should be kept to the minimum necessary to solvate the impurities. Generally, alcohol may be employed in amounts from about 5 to about 25 weight percent of the basic solution. Suitable water soluble alcohols include the lower aliphatic alcohols such as methanol, ethanol, isopropyl alcohol, mixtures thereof, and the like. Isopropyl alcohol is preferred.

After the isomer mixture of bisphenol sulfone is dissolved in the basic aqueous solution, acid is added to the isomer solution to selectively precipitate 4,4' bisphenol sulfone. The amount of acid added in the recovery process according to the present invention is less than that necessary to neutralize the isomer solution. Generally, to achieve selective recovery of 4,4' bisphenol sulfone from isomer mixtures of bisphenol sulfone, less than 1 equivalent of acid is added per mole of 4,4' bisphenol sulfone present in the isomer solution. Preferably, the amount of acid added is from about 0.85 to about 0.95 equivalents per mole of 4,4' bisphenol sulfone. The greater the amount of acid employed the greater is the coprecipitation of 2,4' isomer. If acid is added to neutralize the basic aqueous isomer solution, substantial amounts of 2,4' bisphenol sulfone impurity are coprecipitated with the desired 4,4' bisphenol sulfone resulting in a recovered product of less than desirable purity. On the other hand, if significantly less than 1 equivalent of acid is added, the amount of 4,4' bisphenol sulfone of improved impurity recovered is reduced and the process becomes inefficient for commercial purposes.

The basic aqueous solution of mixed isomers should not be neutralized by the addition of the acid; i.e. the pH should remain above 7. Reducing the pH of the solution to 7 or below results in recovery of 4,4' bisphenol sulfone containing undesirable amounts of 2,4' isomer impurity.

It has been found that the addition of acid in the amount of about 0.9 equivalents per mole of 4,4' bisphenol sulfone provides a commercially optimal balance of high recovery of 4,4' bisphenol sulfone (e.g. yields greater than 75 percent) with high purity (e.g. less than two percent 2,4' bisphenol sulfone impurity). With this amount of acid, the pH of the solution is generally about 9.

Suitable acids include organic and inorganic acids such as acetic, formic, hydrochloric, sulfuric, mixtures thereof, and the like. Mild acids such as acetic and formic acid are preferred.

Preferably the aqueous solution of mixed bisphenol sulfone isomers is cooled simultaneously with, or preferably subsequent to, the acid addition. With cooling, additional 4,4' bisphenol sulfone generally precipitates from solution. Though the aqueous suspension of 4,4' bisphenol sulfone may be cooled to ambient temperatures, it is preferred that the temperature remain above about 60° C. until the precipitated 4,4' bisphenol sulfone crystals are removed. At lower temperatures, it is possible that an undesireable amount of 2,4' bisphenol sulfone may not remain in solution and may co-deposit with the desired 4,4' bisphenol sulfone.

The precipitated 4,4' bisphenol sulfone product is then separated from the aqueous solution by any suitable means such as vacuum filtration, pressure filtration, centrifugation or the like. It is preferred that during the separation the solution be maintained at temperatures of at least 40°-60° C. in order to prevent precipitation of 2,4' isomer onto the 4,4'bisphenol sulfone crystals.

Thereafter, the recovered product may be washed with water to remove traces of the aqueous solution and impurities. Generally, about twice as much wash water is employed as there is bisphenol sulfone, on a weight basis. The wash water should preferably be hot (at least 40° to 50° C.) so as to more readily dissolve and remove 2,4' bisphenol sulfone and impurities that may be on the surfaces of the 4,4' bisphenol sulfone crystals. The recovered 4,4' bisphenol sulfone then may be dried to a powder.

4,4' bisphenol sulfone is recovered from a single aqueous recrystallization in accordance with the process of this invention in high yields and in a state of purity sufficiently high for its general application as a monomer in high molecular weight polymerizations. Typically, more than 75% of the 4,4' bisphenol sulfone present in the isomer mixture is recovered at a purity that exceeds 98%. If, however, even higher purity is desired the process may be repeated on the recovered 4,4' bisphenol sulfone.

An optional step in the recovery process according to the present invention involves contacting activated carbon with the basic aqueous solution of mixed bisphenol sulfone isomers prior to the acid addition. Activated carbon is a purifying agent which is known to be useful in removing impurities such as quinone-type coloring agents and the like from bisphenol sulfone mixtures. Activated carbon can be added directly to the isomer solution in an amount sufficient for the impurities to be adsorbed by the activated carbon. About one to five weight percent activated carbon is normally sufficient. After the activated carbon has been in contact with the solution at elevated temperatures for a period of time sufficient to adsorb the impurities (generally, at least about one minute), it is readily removed by filtration or the like. Thereafter, the inventive process proceeds with the addition of acid to the basic aqueous mixed isomer solution.

In addition to, or in lieu of, activated carbon, other purifying agents such as iron, aluminum, and titanium salts, and charcoal may be added and removed in the same manner as activated carbon. Alternatively, the basic isomer solution can be passed through a fixed bed of activated carbon or other purifying material.

A preferred process of this invention includes dissolving the 4,4' and 2,4' bisphenol sulfone isomer mixture by adding thereto a hot (i.e. 90° C.) dilute aqueous solution of sodium hydroxide in an amount such that the resulting ratio of bisphenol sulfone to sodium hydroxide is about 1:1 on a molar basis and the ratio of water to bisphenol sulfone is about 5:1 on a weight basis. To the resulting homogeneous solution is added glacial acetic acid at a ratio of about 0.9 moles per mole 4,4' bisphenol sulfone. The temperature of the solution is then reduced to about 65° C. The 4,4' bisphenol sulfone precipitate is separated from the liquid by centrifuge, washed with water at about 50° to 60° C., and then dried.

The following examples are provided to illustrate the present invention. The examples are not to be construed as limiting the invention as it will be readily apparent to one skilled in the art that various modifications can be made in the examples in accordance with the principles of the present invention.

EXAMPLE 1

Bisphenol sulfone was synthesized by reacting phenol and sulfuric acid in the presence of ortho-dichlorobenzene solvent to yield one hundred and six grams of wet cake. This material was analyzed by liquid chromatography and two bisphenol sulfone isomers were detected. The composition of the bisphenol sulfone was 93.5 weight percent 4,4' bisphenol sulfone and 6.5 weight percent 2,4' bisphenol sulfone.

The by-products present could not be detected by the liquid chromatography technique. Accordingly, the cake was treated as if it were 93% bisphenol sulfone and 7% ortho-dichlorobenzene by weight.

Sodium hydroxide was added, in the ratio of 1 mole sodium hydroxide per mole of bisphenol sulfone (15.84 gm of sodium hydroxide), to 500 gm of deionized water and the resulting basic solution was heated to 90° C. The wet bisphenol sulfone cake was added to the sodium hydroxide solution and the solution was maintained at 90° C., resulting in complete dissolution of the sulfone cake except for dispersed drops of ortho-dichlorobenzene. Thereafter, 21.11 gm of glacial acetic acid were added to the solution in the ratio of 0.95 mole acetic acid per mole of 4,4' bisphenol sulfone while the solution was agitated with a magnetic stirrer bar. A white precipitate formed when about 75% of the acid had been added. The suspension was cooled to 20° C. over 1 hour and vacuum filtered. The filter cake was washed with water and vacuum dried.

Liquid chromatographic analysis of the precipitate showed that the composition of the cake was 98.2 weight percent 4,4' bisphenol sulfone and 1.8 weight percent 2,4' bisphenol sulfone. The weight of the precipitate was 72.7 gm. This represented a yield of about 74% of the total bisphenol sulfone, and about 77% of the 4,4' bisphenol sulfone, present in the original wet cake.

The aqueous liquor from this precipitation was analyzed by mixing it with an additional 2.64 gm of acetic acid at 90° C. and then cooling the resulting solution to 20° C. The precipitate that formed was filtered and the cake was washed with water and vacuum dried. The composition of this cake, as determined by liquid chromatography, was 3.92 weight percent 4,4' bisphenol sulfone, 6.4 weight percent 2,4' bisphenol sulfone, and 89.68 weight percent unidentified impurities.

EXAMPLE 2

A commercially available bisphenol sulfone was determined by liquid chromatography to comprise 88.19 weight percent 4,4' bisphenol sulfone and 11.81 weight percent 2,4' bisphenol sulfone.

Two hundred grams of this material were added to a solution consisting of 31.96 gm of sodium hydroxide and 1031.96 gm of water at 90° C. The bisphenol sulfone dissolved entirely at 90° C. The sodium hydroxide is believed to have substantially converted the bisphenol sulfone to the monosodium salt of the material. Acetic acid to 95 mole percent of the 4,4' isomer content of the bisphenol sulfone was added (40.17 gm of acid) and this resulted in a white precipitate which persisted as a solid after 75% of the acid had been added. The slurry was cooled to 40° C. and was vacuum filtered. The filter cake then was washed with an equal volume of deionized water and dried.

The composition of the cake, as determined by liquid chromatography, was 98.43 weight percent 4,4' bisphenol sulfone and 1.57 weight percent 2,4' bisphenol sulfone. The dried precipitate was 151.2 gm in weight. This is 75.6% of the bisphenol sulfone, and 84.6% of the 4,4' bisphenol sulfone, present in the starting material.

EXAMPLE 3

A commercially available bisphenol sulfone was determined by liquid chromatography to comprise 89.62 weight percent 4,4' bisphenol sulfone and 10.38 weight percent 2,4' bisphenol sulfone.

378.9 grams of this material were added to a solution consisting of 60.56 gm of sodium hydroxide and 1956.6 gm of water at 90° C. The pH of this solution was 11. The bisphenol sulfone dissolved entirely at this temperature and the bisphenol sulfone was believed to be substantially in the form of the monosodium salt. Acetic acid to 90 mole percent of the 4,4' isomer content was added (73.26 gm of acid). This resulted in a precipitate at 90° C. The pH of the liquor of the resulting slurry was 9.

The slurry was cooled to 60° C. and vacuum filtered. The filter cake was washed with an equal volume of water and dried.

The composition of the cake, as determined by liquid chromatography, was 99.5 weight percent 4,4' bisphenol sulfone and 0.5 weight percent 2,4' bisphenol sulfone. The dried precipitate was 263.8 gm. This was 69.6% of the bisphenol sulfone, and 77.7% of the 4,4 bisphenol sulfone, present in the starting material.

EXAMPLE 4

Bisphenol sulfone was synthesized from phenol and sulfuric acid in ortho-dichlorobenzene to yield 228.5 gm of wet cake. The composition of the bisphenol sulfone content of the cake was 95.3 weight percent 4,4' bisphenol sulfone and 4.7 weight percent 2,4' bisphenol sulfone.

The by-products present could not be detected by the gas chromatograph technique used. The cake was therefore treated as if it were 93% bisphenol sulfone and 7% ortho-dichlorobenzene.

67.92 gm of a 50% aqueous solution of sodium hydroxide (1 mole sodium hydroxide per mole of bisphenol sulfone) and 1062.5 gm of water were placed in a 2 liter beaker and the wet cake added to it. The material was agitated by a stirrer bar and heated to 90° C. Virtually all the bisphenol sulfone dissolved, but to cause complete dissolution, 0.86 gm of a 50% aqueous solution of sodium hydroxide was added at 90° C. 44.19 gm of glacial acetic (90 mole % of the dissolved 4,4' bisphenol sulfone) were added to the mixture over 10 seconds, causing an immediate white precipitate. Agitation of the slurry continued while cooling it to 65° C. The suspension was then vacuum filtered and the resulting cake was washed with 500 ml of water at 25° C.

Gas chromatographic analysis of the wet cake determined that its bisphenol sulfone content was 99.1 weight percent 4,4' bisphenol sulfone and 0.9 weight percent 2,4' bisphenol sulfone. The weight of the dried material was 156.8 gm. This was 74% of the bisphenol sulfone, and 77% of the 4,4' bisphenol sulfone, present in the starting material.

The aqueous liquor from the precipitation was analyzed by mixing it with 7.39 gm acetic acid at 25° C., causing further precipitation. The crystals were separated from the liquor by vacuum filtration, washed with 20 ml of water and dried. Total weight of this material was 29.0 gm. The composition of this material, as determined by gas chromatography, was 94.8 weight percent 4,4' bisphenol sulfone and 5.2 weight percent 2,4' bisphenol sulfone.

What is claimed is:

1. A process for the recovery of 4,4'-bisphenol sulfone from an isomer mixture comprising 4,4'-bisphenol sulfone and 2,4'-bisphenol sulfone, which process comprises dissolving the isomer mixture in a basic aqueous solution comprising about one mole of base per mole of the mixture of 4,4'-bisphenol sulfone and 2,4'-bisphenol sulfone to form a basic isomer solution and adding acid to the isomer solution in an amount of from about 0.85 to 0.95 mole per mole of the 4,4'-bisphenol sulfone wherein said acid is added in an amount sufficient to cause selective precipitation of crystals of 4,4'-bisphenol sulfone yet in an amount less than sufficient to neutralize the isomer solution and removing the crystals of 4,4'-bisphenol from the aqueous solution.

2. The process of claim 1 wherein the basic aqueous solution is maintained at a temperature at least above about 60° C. while dissolving the isomer mixture therein.

3. The process of claim 2 wherein the temperature of the basic aqueous solution is maintained below but near its boiling point while dissolving the isomer mixture therein.

4. The process of claim 3 further comprising cooling said isomer solution to a temperature from about 60° to about 90° C. simultaneously with or subsequent to adding the acid.

5. The process of claim 1 wherein the isomer mixture is comprised of at least about 90 weight percent 4,4' bisphenol sulfone.

6. The process of claim 1 wherein the basic aqueous solution includes a water soluble alcohol.

7. The process of claim 1 further comprising contacting the isomer solution with activated carbon for at least about 1 minute and thereafter adding the acid.

8. A process for the recovery of 4,4' bisphenol sulfone from an isomer mixture comprising 4,4' and 2,4' isomers of bisphenol sulfone, which process comprises:
   (a) dissolving the isomer mixture in a basic aqueous solution comprising about 1 mole of base per mole of bisphenol sulfone to form an isomer solution; said aqueous solution being in an amount about five times the weight of the isomer mixture and being at a temperature of about 90° C.;

(b) adding to the isomer solution about 0.9 equivalents of acid per mole of the 4,4' bisphenol sulfone to form a suspension comprising crystals of 4,4' bisphenol sulfone;

(c) cooling the suspension to about 65° C.; and (d) removing the crystals of 4,4' bisphenol from the suspension.

* * * * *